United States Patent [19]

Giuffre et al.

[11] Patent Number: 4,880,413
[45] Date of Patent: Nov. 14, 1989

[54] SHARP INSTRUMENT PROTECTION MEANS

[76] Inventors: Kenneth A. Giuffre; Michele A. Giuffre, both of 201 Sagamore La., Franklin Lakes, N.J. 07417

[21] Appl. No.: 152,167
[22] Filed: Feb. 4, 1988
[51] Int. Cl.⁴ .............................................. A61M 5/32
[52] U.S. Cl. ..................................... 604/192; 604/263
[58] Field of Search ................................. 604/192, 263

[56] References Cited

U.S. PATENT DOCUMENTS 4,559,042 12/1985 Votel ..................................... 604/192
4,610,667 9/1986 Pedicano et al. ..................... 604/263
4,742,910 5/1988 Staebler ............................. 604/192 X

FOREIGN PATENT DOCUMENTS 3433359 4/1986 Fed. Rep. of Germany ...... 604/192

Primary Examiner—John D. Yasko
Attorney, Agent, or Firm—Brumbaugh, Graves, Donohue & Raymond

[57] ABSTRACT

A cover for protecting sharp medical instruments, such as needles and syringes, includes a shield, a tapered hollow body which permits a sharp instrument to be guided toward an interior of the cover and an annular stabilization means provided at a smaller diameter end of the cover which sealingly engages the instrument to prevent the transverse motion thereof.

3 Claims, 1 Drawing Sheet

SHARP INSTRUMENT PROTECTION MEANS

BACKGROUND OF THE INVENTION

The present invention relates to a protective cover for medical instruments such as hypodermic syringes and in particular to an improved cover design which significantly increases the area of initial contact between the instrument and the cover.

There exists a need to protect health personnel from diseases transmissible through accidental injury incurred in the use of sharp instruments, including hollow needle devices. Such diseases include human immunodeficiency virus (HIV), hepatitis B, non A non B hepatitis, and others. Sharp instruments currently in use in the health field commonly utilize a cover which serves the dual purpose of maintaining sterility of the instrument while also protecting the user from unintentional self-injury. Many times, injury is inflicted when the user attempts to replace the cover over the sharp instrument after its use on a patient. Because of the limited diameter of the protective cover, the instrument will pass outside the lumen and, pierce the fingers, gloved or ungloved, of the user. This endangers the user through risk of transmission of several blood or body-fluid-born disease agents which may be present in the blood and (or) body fluids of the patient.

SUMMARY OF THE INVENTION

To help minimize this risk, it is an object of the present invention to provide a device which, by its tapered diameter and shape, can facilitate replacement of a sharp medical instrument within a cover while lessening the danger that the instrument will pass outside the cover and pierce the hands or fingers of the user, or come in direct contact with them.

In accordance with the present invention, this and other objects are achieved by a cover for protecting sharp medical instruments, such as needles and syringes, which includes a large diameter guide portion for guiding the sharp instrument toward an interior of the cover and an annular stabilization means provided at a smaller diameter end of the cover which sealingly engages the instrument to prevent transverse motion therein.

For a better understanding of the invention, as well as other objects and further features thereof, reference is had to the following detailed description of the preferred embodiments taken in conjunction with the accompanying drawings.

DESCRIPTION OF THE PREFERRED EMBODIMENT

Figure 1:
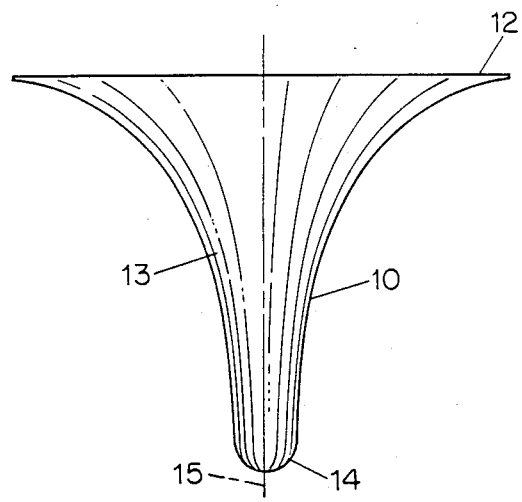
FIG. 1 is a plan view of one embodiment of the sharp instrument protection means according to the present invention.
Figure 2:
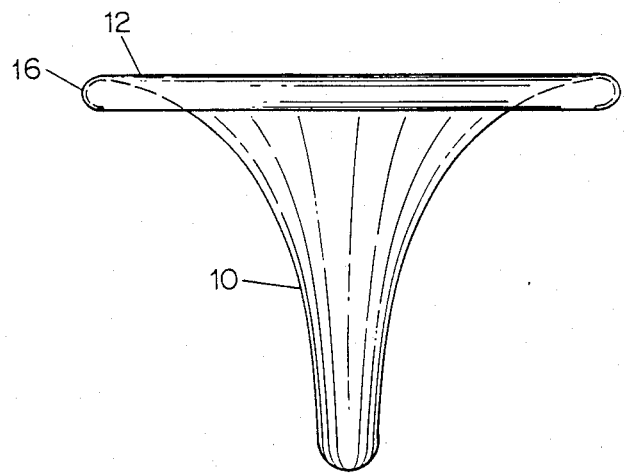
FIG. 2 shows an alternate embodiment of a guide portion of the sharp instrument protection means of FIG. 1.

In FIG. 1, there is shown a medical instrument cover or housing 10 provided with a first circular shield 12 and a hollow body 13 which tapers inwardly to nipple-shaped end 14. Preferably, the diameter of the shield 12 is chosen so as to cover the surface area of a hand, i.e. in the shape of a fist, or at least two fingers when the user grasps the nipple end 14 of the cover 10. The body 13 is contoured asymptotically from the shield 12 along the center imaginary line 15 of the nipple-shaped end 14. The diameter of nipple-shaped end 14 is preferably chosen in accordance with the particular sharp instrument intended to be housed therein. As shown in FIG. 2, the circular shield 12 of the cover 10 can also be formed with an upwardly or downwardly curved edge portion 16 rather than the flat circular shape shown in FIGS. 1 and 3.

Figure 3:
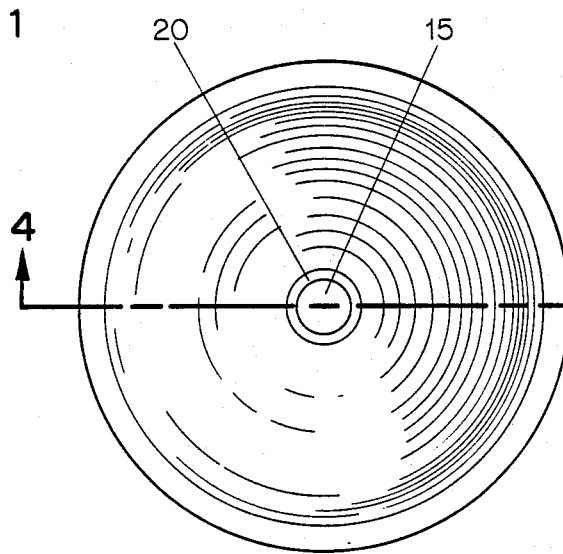
FIG. 3 is a top view of the embodiment shown in FIG. 1.
Figure 4:
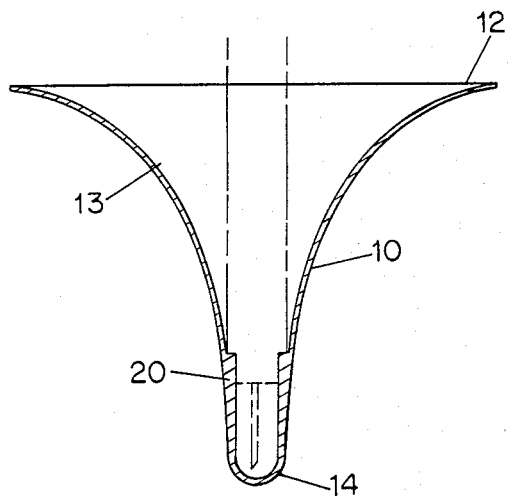
FIG. 4 is a sectional view along line I—I of FIG. 3.

Referring to FIGS. 3 and 4, a stabilization insert 20 is shown axially disposed within the body of the cover 10 at the smaller diameter end 14. The insert 20 may be integrally formed with the cover 10 and its length and width are preferably chosen so as to accommodate the end of the sharp instrument within the space intermediate its axial walls such that the sharp instrument does not approach the curved edge of the nipple-shaped end 14. Insert 20 may accommodate the needle by means of a snap engagement or may be internally threaded to accommodate screw-type configurations. The latter configuration is particularly useful in instruments such as syringes having detachable, disposable portions coupled to a reusable structure. Alternatively, the insert 20 may consist of a pliable compound, such as latex rubber that will allow for penetration by any sharp instrument that fits within the cover 10.

The curved body 13 of the cover 10 functions to guide an end of the sharp instrument toward a secure engagement within the insert 20. The shield 12 permits less precision on the part of the user in guiding the instrument into the cover 10, thereby significantly decreasing the chance of the instrument contacting or piercing the skin.

Figure 5:
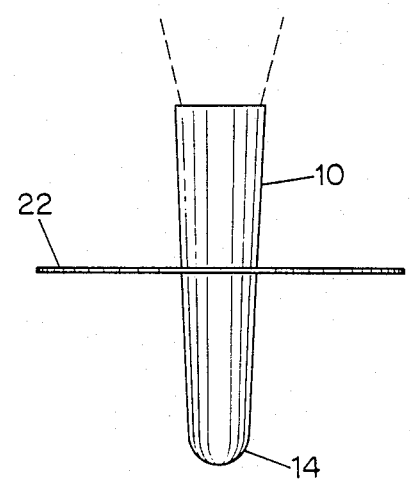
FIG. 5 is a plan view of another embodiment of the device demonstrating a variation in shield placement.

Referring now to FIG. 5, another embodiment of the invention is shown wherein a circular shield portion 22 is axially displaced towards the smaller diameter end 14. The housing 10 is of a slightly tapered tubular shape having a smaller diameter end 14 configured as in the embodiment of FIG. 1.

The detailed description of the preferred embodiment of the invention having been set forth herein for the purpose of explaining the principles thereof, it is known that there may be modifications, variation or change in the invention without departing from the proper scope of the invention and the claims thereto.

We claim:

1. A disposable protective cover for an injection syringe, for receiving said syringe and preventing injury to the user after use thereof, comprising a housing member with circular symmetry about a longitudinal axis and having a first open axial end and a second closed axial end, said housing member having a hollow cavity extending from said open axial end, said cavity having a guiding portion adjacent said open end in the form of a continuously curved funnel opening, said funnel opening having interior walls being continously curved to be almost perpendicular to said axis at said open end and substantially paralled to the axis beginning at a point closer to the closed axial end of the funnel than to the open end of the funnel said cavity having a cylindrically shaped syringe retaining portion extending from said point to said closed end of said housing, the wall of said syringe retaining portion being radially thickened inwardly at least at said point to thereby form an interior step and configured throughout its length to grip and retain an inserted syringe.

2. A cover in accordance with claim 1, wherein an inner face of said syringe retaining portion is threaded so as to threadedly engage an inserted syringe.

3. The disposable protective cover according to claim 1, wherein said syringe retaining portion is formed of a material substantially more pliable than said first guiding portion to elastically surround and grip the housing of an inserted syringe.

* * * * *